United States Patent [19]

Schwippert

[11] 4,438,749

[45] Mar. 27, 1984

[54] FUEL SUPPLY SYSTEM FOR COMBUSTION ENGINES

[75] Inventor: Guusstaaf A. Schwippert, Pijnacker, Netherlands

[73] Assignee: Nederlandse Centrale Organisatie Voor Toegepast-Natuurwetenschappelijk Onderzoek, The Hague, Netherlands

[21] Appl. No.: 283,607

[22] Filed: Jul. 15, 1981

[30] Foreign Application Priority Data

Jul. 15, 1980 [NL] Netherlands .......................... 8004071

[51] Int. Cl.³ .......................... F02D 1/00; F02B 3/00
[52] U.S. Cl. .................................. 123/494; 123/381; 356/133
[58] Field of Search ............... 123/494, 434, 474, 478, 123/438, 537, 381, 357; 356/133

[56] References Cited

U.S. PATENT DOCUMENTS

| | | | |
|---|---|---|---|
| 2,964,993 | 12/1960 | Witt . | |
| 2,996,053 | 9/1961 | Evans | 123/381 |
| 3,071,038 | 1/1963 | Vollmer | 356/133 |
| 3,282,149 | 11/1966 | Shaw et al. | 356/133 |
| 3,520,619 | 7/1970 | Ward | 356/133 |
| 3,750,635 | 8/1973 | Hoffman et al. | 123/357 |
| 3,982,503 | 9/1976 | Keranen | 123/494 |
| 3,999,857 | 12/1976 | David et al. | 356/133 |
| 4,031,864 | 6/1977 | Crothers . | |
| 4,252,097 | 2/1981 | Hartford et al. | 123/381 |
| 4,306,805 | 12/1981 | Arrington | 356/133 |

FOREIGN PATENT DOCUMENTS

| | | |
|---|---|---|
| 2544444 | 4/1977 | Fed. Rep. of Germany . |
| 2713775 | 10/1978 | Fed. Rep. of Germany . |
| 2409389 | 6/1979 | France . |
| 1561668 | 2/1980 | United Kingdom . |

Primary Examiner—Raymond A. Nelli
Attorney, Agent, or Firm—Watson, Cole, Grindle & Watson

[57] ABSTRACT

A fuel supply system for fuels, among which hydrocarbons, such as gasoline, alcohols or other fuel, or a mixture thereof, for combustion engines, provided with a device to determine the instantaneous state or composition of the fuel and to emit a signal as a variable for the control of the dosage device of the air-fuel ratio, comprising an opto-electronic sensor mounted in the fuel to measure its index of light refraction, and an electronic circuit connected to the sensor to control the dosage device in accordance with the determined state or composition.

7 Claims, 7 Drawing Figures

FUEL SUPPLY SYSTEM FOR COMBUSTION ENGINES

This invention relates to a fuel supply system for fuels, among which hydrocarbons, such as gasoline, alcohols or other fuel, or a mixture thereof, for combustion engines, provided with a device to determine the instantaneous state or composition of the fuel and to emit a measuring signal as a variable in order to control the dosage device of the air-fuel ratio. Such a fuel supply system is known from the Dutch patent application No. 77,12689.

For combustion engines using gasoline or diesel oil as fuel, also fuel mixtures can be applied which consist of hydrocarbon of a type, such as gasoline or diesel, and a alcohol of a type, such as methanol or ethanol. The correct operation of such an engine which is provided with a carburetor or injection device, strongly depends on the precise fuel-air ratio. In case the state or the composition of the fuel supplied from the fuel tank is unknown, then only an adjustment can be approximately attained in which the engine still has a reasonable performance possibly at the expense of a high fuel consumption. By "state" one understands the fluid or gaseous state of agregation or combination thereof of one or a plurality of fuels. In order to be able to supply the optimum fuel-air mixture to the engine, the dosage device required for this has to be continuously adjusted on the basis of a continuous measurement of the state or composition of the fuel.

The measurement required for this purpose is realized in the known system from above mentioned patent application with the aid of a dielectric sensor which continuously determines the dielectric Properties of the fuel. This dielectric sensor, however, is strongly sensitive to side influences, such as temperature and flow velocity. Also this sensor required relatively complicated apparatus and circuits.

This invention aims to obviate said problems by the application of a sensor of an other type, the construction of which and the required electronic circuit are relatively simple.

In accordance with the invention this is obtained with a fuel supply system of the type mentioned in the preamble by an opto-electric sensor, positioned in the fuel, for measuring its index of light refraction, and by an electronic circuit connected to the sensor for controlling the dosage device in accordance with the determined state or composition.

A further object of the invention is to provide an opto-electronic sensor consisting of a light source, a light conductor being arranged at least partially in contact with the fuel, and a light receiver, the measurement of the index of light refraction being based on a limited-angle measurement, and the quantity of light taken up by the light receiver at least comprises a variable portion due to non-direct irradiation and dependent on the index of refraction of the fuel mixture. The light conductor can consist of a bar of glass, on the ends of which the light source and light receiver respectively are mounted.

As the opto-electric sensor in accordance with the invention is somewhat temperature dependant, an additional light receiver or photo transistor can be positioned adjacent the light source to maintain constant the quantity of light emitted by the light source and to control accordingly the current of the light source with the aid of the electronic circuit. A temperature detecting element can also be positioned in the supply line of the fuel mixture and be connected to the electronic circuit for correcting the measured index of refraction and therewith the controlling signal of the control of the dosage device.

It may be required with certain fuel compositions, such as 0–50% gasoline and 100–50% alcohol, to preheat the fuel mixture to about 45° C. in order to avoid ice formation during evaporation of the mixture in the carburetor. For this purpose the mounted temperature detecting element and associated electronic circuit are advantageously used within the frame work of the temperature control for controlling a valve in the supply water line of a heat exchanger taken up in the supply line. The casing of said heat exchanger is taken up in the circuit of the cooling water of the engine.

The invention will further be elucidated, by way of example, on the basis of an embodiment with reference to the drawings, in which.

Figures 1, 5:
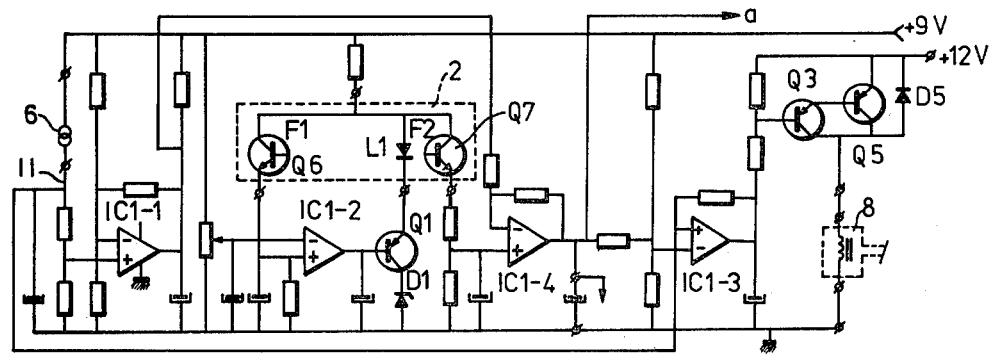
Figures 2, 5:
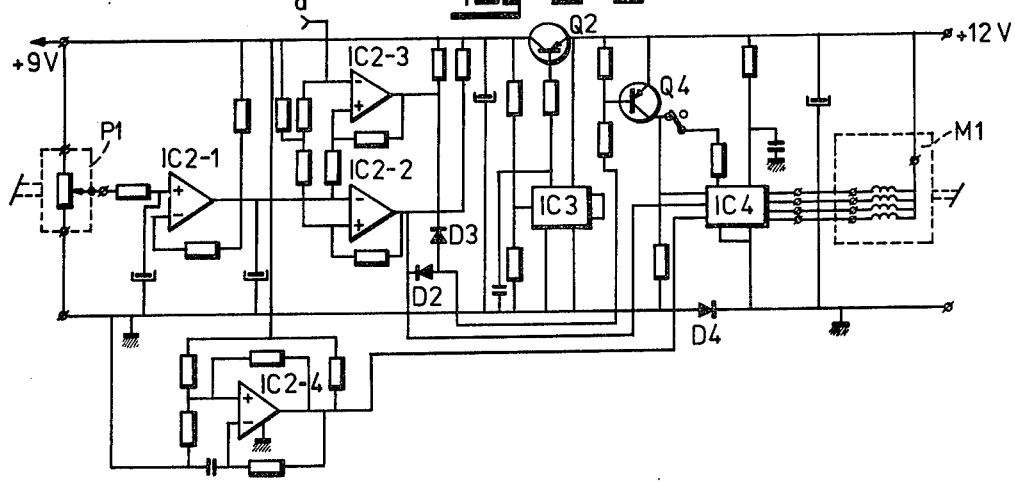

FIGS. 5.1 and 5.2 show a diagram of the electronic circuit; and

Figure 6:
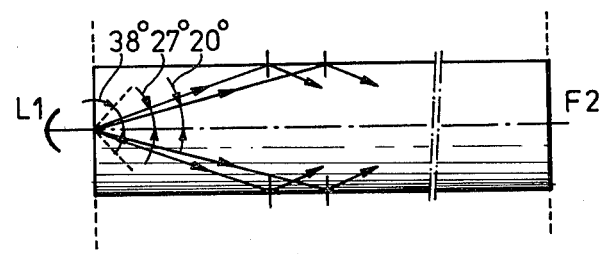
Figure 6:
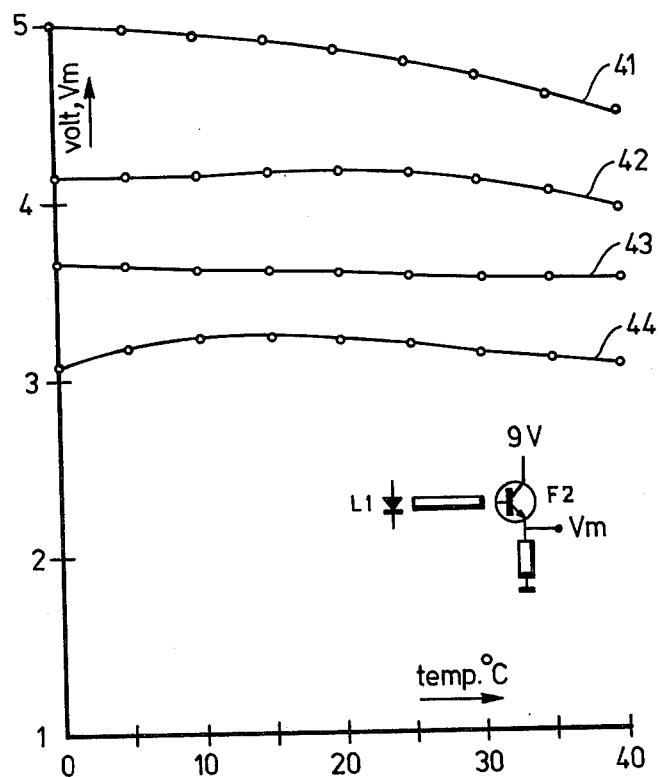

FIG. 6 shows a graph to elucidate the temperature dependency of the measured voltages in the circuit for several fuel mixture compositions.

Figure 1:
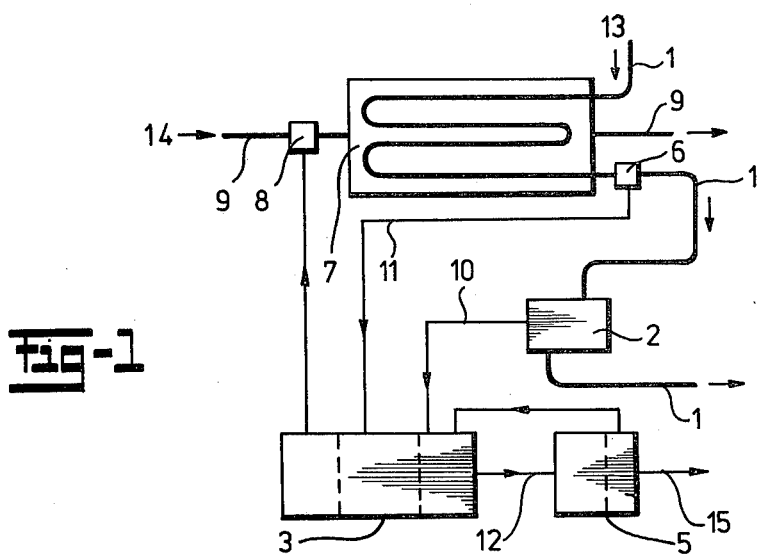
FIG. 1 shows a schematic view of the fuel supply system of the invention.

Referring to FIG. 1, the fuel 13 in said fuel supply system is supplied by means of a non-indicated fuel pump via line 1 to a dosage device, such as a carburetor or injection device. Said line 1 first passes a heat exchanger 7, at the end of which the temperature of the fuel is measured with a temperature detecting element 6. The fuel then is conducted past the opto-electronic sensor 2 and subsequently is supplied outside the system to the carburetor or injection device. The opto-electronic sensor determines the percentage of alcohol, such as methanol or ethanol, in the fuel mixture or determines the state of agregation of the fuel and emits an output signal via the lead 10 to the electronic circuit 3. The output signal of this circuit controls a servo-motor 5, having a position feedback, which motor for example via a bowden cable 15 controls the adjustment of the jet needles in the carburetor. The whole system may be implemented as a so called "retrofit".

The possibly required pre-heating of the fuel mixture in the heat exchanger is realized by means of the cooling water from the cooling circuit of the engine, the temperature of which during driving may amount to a maximum of 90° C. The heat exchanger consists of a cylindric casing in which a pipe having a length of 1,25 meter is folded, which casing is connected to the circuit of the cooling water by means of a supply valve 8. The electronic circuit controls the position of the supply valve 8 in reaction to the signal emitted by the temperature detecting element 6 via the lead 11.

Figure 2:
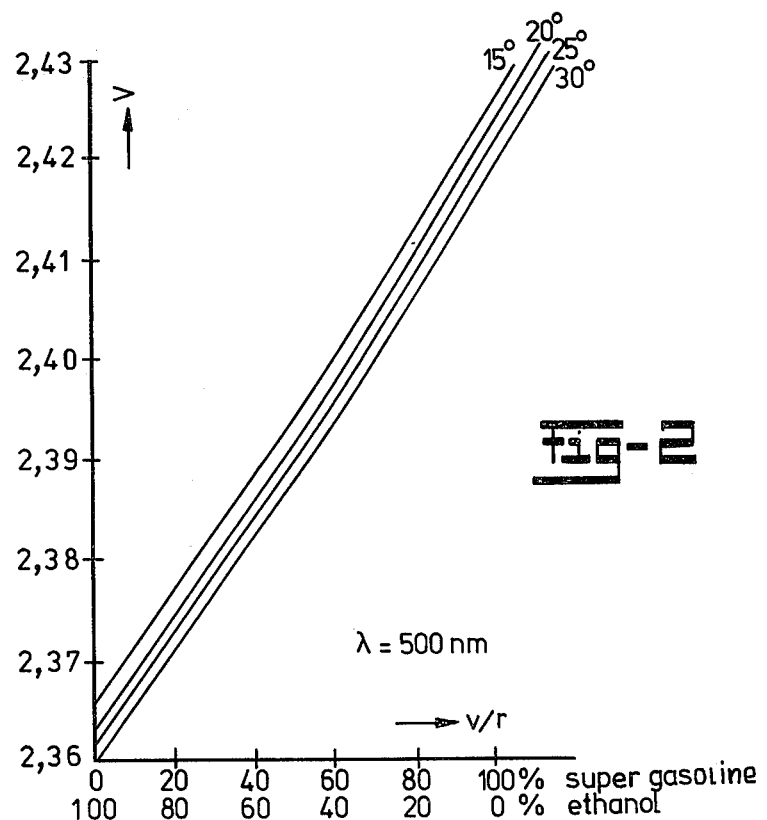
FIG. 2 shows a graph of the output voltage of the sensor in relation to the fuel composition at different temperatures as parameter.

Referring to FIG. 2, the output voltage of the sensor by way of example is indicated as a function of the composition super gasoline-ethanol having as parameter the temperature 15°, 20°, 25°, 30°. The output voltage indicated along the ordinate has a direct relation to the measured index of refraction of the mixture. The extreme values of the index of refraction of the blend super gasoline-ethanol are $\eta=1,43$ for 100% super gasoline; $\eta=1,36$ for 100% ethanol; and $\eta=1,33$ for 100% methanol.

Figure 3:
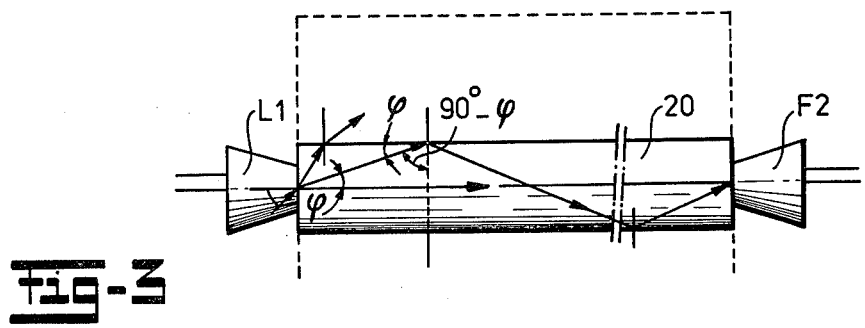
FIG. 3 shows the measuring principle of the opto-electronic sensor.

The measuring principle of the opto-electronic sensor is generally indicated in FIG. 3. A light conductor, a light source such as an infrared light emitting diode, and a photo transistor are designated as reference numbers 20, L1 and F2 respectively. The index of refraction is measured with a so called critical-angle measurement, whereby a bar of glass may advantageously be used for the light conductor. The light source is mounted at one side by means of a suitable adhesive, and an associated light receiver, such as a photo transistor, is similarly mounted at the other side. The ends of said bar are contained in air, while the portion therebetween is in contact with or is washed by the fuel mixture to be watched. A bar of glass is selected as light conductor as it has been proved that a plastic conductor (acryl) is corroded by the corrosive fuel mixture, and is more sensitive than glass to scale due to the surface being less smooth. Said bar form is not specifically required and curved conductors, such as glass fibers, can be used as well.

The light rays in the glass are conveyed to the light receiver either directly or after refraction, or they get lost by going out to the surrounding medium of the fuel. The quantity of light received in the light receiver consists of a fixed portion resulting from direct irradiation and direct transmission from source to receiver and of a variable portion resulting from non-direct irradiation of light which after refraction is brought back in the glass.

In FIG. 3 it is indicated as to how the path of the light rays from the light source can run. The index of refraction $\eta_1$ of glass is about 1,52 (normal glass) and the index of refraction $\eta_2$ of the surrounding fuel mixture, consisting of super gasoline and ethanol, is between about 1,36 and 1,43. According to the law of Snellius the angle $\phi$, whereby the light falling upon a boundary plane of two media and still wholly being reflected, which means in this case staying within the bar of glass, is given by sin $(90°-\phi)=\eta_2/\eta_1$.

For 100% ethanol (E) $\phi$ becomes $\phi=27°$ in accordance with sin $(90°-\phi)=1,36/1,52=0,89$. All light rays having a $\phi>27°$ are lost for the photo detector.

For 100% super gasoline (SB) $\phi$ becomes $\phi=20°$ in accordance with sin $(90°-\phi)=1,43/1,52=0,94$. All light rays having a $\phi>20°$ are lost for the photo detector.

In an example embodiment of the glass bar having a diameter of 5 mm and $\eta_1=1,52$, said light source radiates the light in with an opening angle $\theta$ of maximum 38°. This aperture is calculated from the formula sin $\theta=\sqrt{\eta_1^2-\eta_2^2}$. The desired $\theta$-region is covered in each case.

Assuming that the light source has a uniform distribution of intensity over the aperture of 38° and having a fuel mixture of SB (0-100%)-E (100-0%), now 20/38 part of the quantity of light within the glass tube is conveyed and forms a steady background for the photo transistor independent of $\eta$-alterations of the fuel mixture, and 7/38 part of the irradiated intensity is direct dependant upon the fuel mixture for reflection. The remainder of the irradiated light gets lost by direct transmission to the fuel mixture. This is irrespective of the given $\eta$-values.

The maximum deviation, to be expected in the given conditions, with respect to the steady background (intensity) at the location of the photo transistor consequently is $7/20\times100\%=35\%$ apart from the losses in the glass bar per se. This deviation is well observable with relatively simple means.

In order to safely guarantee the stability of the measurement of the state or composition of the fuel a number of measures can be applied to compensate for the influence of the temperature, namely:

1. The quantity of light irradiated by the light source L1 in the glass bar is guarded by means of a second photo transistor F1 positioned at the side of the LED-light source. The intensity of the light from the light source is temperature dependant in accordance with the normal diode equation. As the desired temperature range is about 60° one has to take care that the intensity of the light after being adjusted to a certain value is maintained. This is realized with the photo transistor F1 which adjusts the current of the light source with the aid of a controlling loop in the electronic circuit.
2. A thermal metallic lead (litze wire or via the housing) between both photo transistors is used to safely guarantee the thermal equality.
3. The temperature of the fuel is measured for correcting the measured index of refraction which is temperature dependant. This correction is provided in the electronic circuit.

Figure 4:
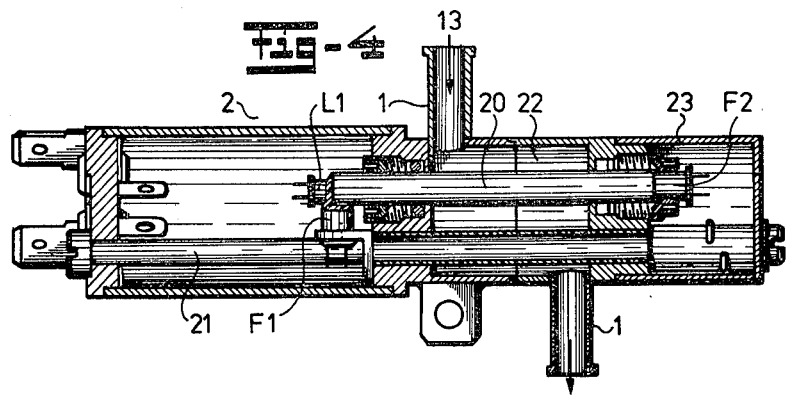
FIG. 4 shows a longitudinal section of the opto-electronic sensor.

In FIG. 4 a longitudinal section is given of the opto-electronic sensor 2. The conduit of the fuel 13 is designated as 1, which fuel at least partially washes the glass bar 20 in the space 22. The light source L1 and the photo transistor F2 are positioned on the one and the other side respectively of the glass bar, the control photo transistor F1 being mounted adjacent the light source L1. The housing of the sensor is designated as 23, through which housing a connection bolt 21 is inserted which can provide for the thermal equality of both photo transistors and also can serve for leading in the connection wires of the photo transistor F2.

It can also be of importance to determine the mutual proportion in ethanol-methanol mixtures for example and to adapt accordingly the carburetor or the injection.

There is an increasing tendency to use LPC(liquefied petroleum gases) or propane/butane as engine fuel. For this purpose said LPG, which is contained in liquid form in the tank, is evaporated via a heat exchanger with cooling water, and is carbureted as support gas. The disadvantage of this carbureting of support gas is that this gas thereby is quite voluminous and therefore causes loss of power. This disadvantage could be obviated if it was carbureted as a liquid. The cooling effect of liquid LPG on the inlet air moreover has a favorable influence on the efficiency.

A fuel like LPG is contained in the tank in a vapour-liquid balance. In case a pressure decrease and temperature changes occur during passage through conduits or controlling apparatus, formation of vapour bubbles occur. The fuel in the conduits or controlling apparatus then is contained in two states of agregation: vapour and liquid. The sensor is capable to detect this and causes the carburetor or injection system to adapt itself thereto. Without such an adaptation the carbureting or injection would be disregulated by the far less fuel contents of the vapour bubbles.

The drawing of the electronic circuit is indicated in FIGS. 5.1 and 5.2, which circuit consists of simple components. The temperature measuring bridge comprising the temperature detecting element 6 and the amplifier IC 1.1 is indicated in the left portion of FIG. 5.1.

The photo transistor F1 inserted for correction purposes controls the diode current of the light source L1 via the amplifier IC 1.2 and the transistor Q1. The signal outputted by the photo transistor F2 is supplied to the one input of the amplifier IC 1.4, to the other input of which the measuring signal of the temperature pick-up 6 is supplied via the amplifier IC 1.1 so as to correct the temperature dependency. The adjustment of this amplifier is such that based upon the measuring value at a certain temperature and a reference fuel, for example 100% ethanol, the influence of the temperature is limited to 5% of the final value.

In FIG. 6 an example is given of the temperature dependancy of the measured voltage for some fuel compositions, namely graph 41 for 100% ethanol, graph 42 for 50% ethanol and 50% normal gasoline, graph 43 for 25% ethanol and 75% normal gasoline, graph 41 for 100% normal gasoline. These graphs after temperature correction extend straight within a tolerance from 5 to 7%.

The measuring signal in FIG. 5.1 then is summed with a reference voltage from a fixed voltage devider and is supplied to the one input of the succeeding amplifier IC 1.3. The temperature signal from the temperature detecting element 6 is supplied to the other input of said amplifier. The signal from the amplifier IC 1.3 is supplied via a power transistor Q3 and Q5 to the proportional valve control 8 of the water conduit 9 of the heat exchanger 7.

The fuel from a fuel composition of 100% ethanol can be heated to 45° C. and the fuel from a fuel composition of 100% gasoline can be preheated to 10° C. Mixtures there between are proportionally regulated between 10° and 45° C. in dependence of the measuring value.

The signal from the output of the amplifier IC 1.4 is also supplied to the electric circuit, indicated in FIG. 5.2, to control the servo-motor M1. This motor may be a step motor having a delay means, which via a bowden-cable mechanism operates the jet adjustment (normal and steady). The measuring value signal is supplied via a left-right control circuit IC 2.2/3 to the control circuit IC 4 of the step motor. The position of the motor axis is reported back with the aid of a coupled linear potentiometer P1 to the amplifier IC 2.1. A voltage stabilization circuit is designated as IC 3. The supply voltage for the electronic circuit is derived from the accumulator of the related motor vehicle.

The length of the glass bar preferably should be 5 cm or somewhat more. The diameter of the glass bar is selected such that an optimum coupling with the light source and photo transistors is obtained. Advantageously a diameter of 5 mm is selected. In order to obtain reproduceable properties of the sensor one has to mount the elements rectangular to the surfaces by means for example of an epoxy adhesive. The most suitable glass appears to be boron-silicate glass having an index of $\eta = 1,49 \ldots 1,52$.

The reproduceability of the measurement of the index of refraction at one and the same temperature while using the same sensor is better than 5%. The electronic circuit is capable to operate within a large range of temperatures.

It is also possible to mount both light source and light receiver at one side, through which the opto-electronic sensor can be introduced as an insertion unit in a fuel conduit. The other end of the light conductor then has to be made reflecting by means of a mirror.

The sensor can also be used in liquid mixtures or blends which adhere to the glass bar, such as for example diesel oil blended with another fuel. The adhesion of said oil to the bar causes a false measurement of the mixture composition. In order to strongly reduce or obviate said adhesion, advantageously use is made of a thin coating for example of a plastic (PTFE) or a metal, which is transparent for the applied type of light. The optical properties of said thin layer have to be such that the operation of the sensor is not essentially affected.

The measuring range of the sensor can be altered by an other election of the material of the glass bar, and also by the selection of another wave length of the light source.

I claim:

1. A device for controlling the air-fuel ratio in a fuel supply system for combustion engines, comprising:
    an opto-electronic sensor for measuring the index of light refraction of the fuel, said opto-electronic sensor including a light source, a light conductor positioned at least partially in contact with the fuel, and a light receiver, whereby the measurement of the index of light refraction is based on a critical-angle measurement, and the quantity of light taken up by the light receiver at least comprises a variable portion resulting from non-direct irradiation and dependent on the index of refraction of the fuel;
    an electronic circuit responsive to said opto-electronic sensor for generating a control signal in accordance with the state of aggregation or composition of said fuel; and
    a temperature detecting element positioned in the fuel supply conduit and connected to said electronic circuit for correcting the measured index of refraction and thereby the control signal in accordance with temperature changes in the supplied fuel.

2. A device as in claim 1 further comprising an additional light receiver mounted adjacent said light source for regulating the quantity of light emitted thereby and including means for adjusting the current of the light source for compensating for the temperature dependency of said opto-electronic sensor.

3. A device as set forth in claim 1 further comprising a heat exchanger positioned in the fuel supply conduit upstream from said temperature detecting element, said heat exchanger including a casing forming part of the cooling water circuit of the engine for pre-heating the fuel and being controlled by the electronic circuit.

4. A device according to claim 3, wherein said light conductor consists of a bar of glass, on each end of which the light source and the light receiver, respectively, are mounted.

5. A device for controlling the air-fuel ratio in a fuel supply system for combustion engines, comprising:
    an opto-electronic sensor for measuring the index of light refraction of the fuel, said opto-electronic sensor including a light source, a light conductor positioned at least partially in contact with the fuel, and a light receiver, whereby the measurement of the index of light refraction is based on a critical-angle measurement, and the quantity of light taken up by the light receiver at least comprises a variable portion resulting from non-direct irradiation and dependent on the index of refraction of the fuel;

an electronic circuit responsive to said opto-electronic sensor for generating a control signal in accordance with the composition or aggregation of said fuel;

an additional light receiver mounted adjacent said light source for regulating the quantity of light emitted thereby and including means for adjusting the current of the light source for compensating for the temperature dependency of said opto-electronic sensor; and a heat exchanger positioned in the fuel supply conduit and including a casing forming part of the cooling water circuit of the engine for pre-heating the fuel and being controlled by the electronic circuit.

6. A device as set forth in claim 5 further comprising a temperature detecting element positioned in the fuel supply conduit and connected to said electronic circuit for correcting the measured index of refraction in accordance with temperature changes in the supplied fuel.

7. A device as set forth in claim 6 wherein said light conductor is a bar of glass on the ends of which said light source and said light receiver are respectively mounted.

* * * * *